United States Patent [19]

Uhler et al.

[11] Patent Number: 4,468,820

[45] Date of Patent: Sep. 4, 1984

[54] HAPTIC ATTACHMENT FOR INTRAOCULAR LENSES

[75] Inventors: Kenneth C. Uhler, Apple Valley; Warren S. West, Burnsville, both of Minn.

[73] Assignee: Precision-Cosmet Co., Inc., Minnetonka, Minn.

[21] Appl. No.: 376,707

[22] Filed: May 10, 1982

[51] Int. Cl.³ .......................... A61F 1/16; A61F 1/24
[52] U.S. Cl. ........................................................ 3/13
[58] Field of Search .................................. 3/13, 1

[56] References Cited

U.S. PATENT DOCUMENTS

| | | | |
|---|---|---|---|
| 2,834,023 | 5/1958 | Lieb | 3/13 X |
| 4,110,848 | 9/1978 | Jensen | 3/13 |
| 4,159,546 | 7/1979 | Shearing | 3/13 |
| 4,174,543 | 11/1979 | Kelman | 3/13 |
| 4,316,293 | 2/1982 | Bayers | 3/13 |

OTHER PUBLICATIONS

Covered Bridge an Update on Lens Implantation or Bridge over Troubled Waters, (3rd Attempt), (Book), by John H. Sheets, M.D., 1977, pp. 5–13.
The Leiske Physioflex, Style 10 Anterior Chamber Lens, (advertisement), Surgidev Corp., 1421 State Street, Santa Barbara, CA, Jan. 4, 1981.
The Lindstrom Centrex, Style 20 Posterior Chamber Lens, (advertisement), Surgidev Corp., Santa Barbara, CA, Jan. 4, 1981.

*Primary Examiner*—Ronald L. Frinks
*Attorney, Agent, or Firm*—Merchant, Gould, Smith, Edell, Welter & Schmidt

[57] ABSTRACT

An intraocular lens (10) adapted for use as artificial lens implant is disclosed. The intraocular lens (10) includes an optical lens body (11) having an convex upper surface (11a) and a bottom surface (11b). The convex surface (11a) has a peripheral zone (15) and an apex (16). The lens body (11) has a height of a distance from the apex (16) to the bottom surface (11b). A haptic element mounting means comprises a first boss (13a) cooperatively connected to the convex surface (11a) within the peripheral zone (15). The first boss (13a) has a height that does not extend substantially above a plane parallel to the bottom surface (11b) and the plane contains the apex (16) of the optical lens body (11). The first boss (13a) does not substantially increase the height of the optical lens body (11). In a preferred embodiment, the intraocular lens (10) includes a first and second haptic element (12a) and (12b) cooperatively connected to the first boss (13a) and second boss (13b). In another embodiment, an intraocular lens (50) includes a lens body (11) and bosses (13a), (13b), (13c), and (13d) cooperatively connected to the convex surface (11a). The haptic elements (52) and (53) are cooperatively connected to the bosses (13a), (13b), (13c) and (13d) and the haptic elements (52) and (53) extend outwardly and downwardly from the lens body (11), wherein the lens (11) is supported in a spaced relation anteriorly to the iris (23) of an eye.

11 Claims, 10 Drawing Figures

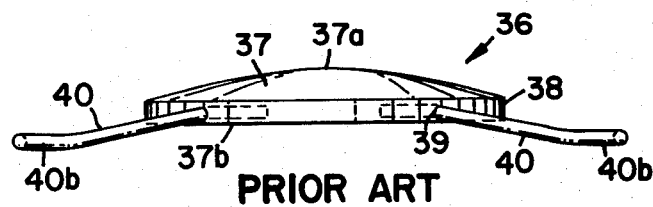
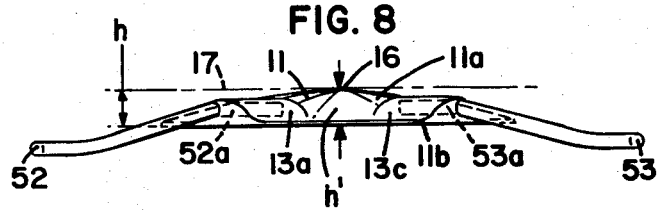
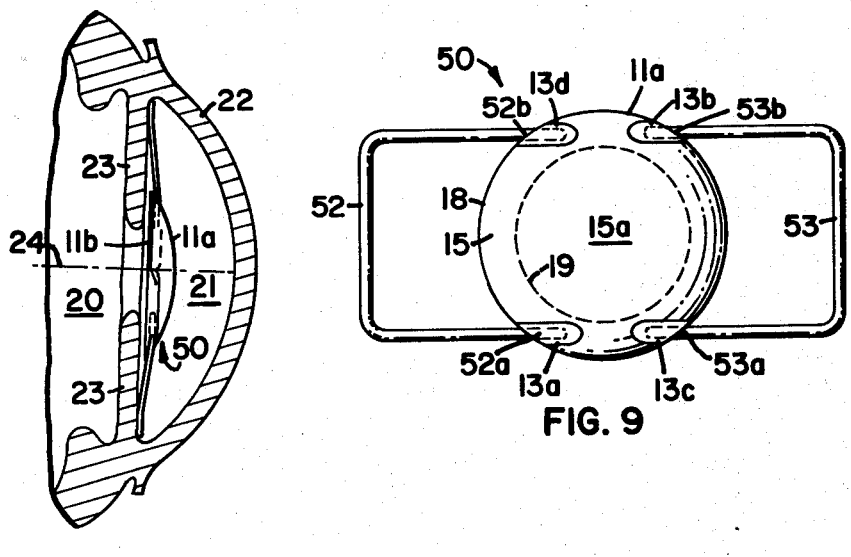

HAPTIC ATTACHMENT FOR INTRAOCULAR LENSES

BACKGROUND OF THE INVENTION

1. Field of the Invention

This invention relates generally to intraocular lenses to be used as artifical lens implants in eyes from which the cataractous natural lens has been removed, and more particularly to an improved attachment system for the haptic elements of an intraocular lens.

2. Discussion of the Prior Art

Intraocular lenses used as artificial lens implants are well-known in the art. One of the factors in determining the length of an incision to be made for insertion of the intraocular lens is the overall height of the lens. Any reduction in the height of the lens would allow for a smaller incision, which is surgically desirable. The smaller the incision that is necessary, the less difficult it is for the post-operative recovery and healing period of the patient. In addition, a thick lens increases the total weight of the lens. Excessive lens weight may contribute to distortion of the pupil or other undesirable effects.

The prior art lenses typically have a base at the bottom of the lens to which the haptic elements are attached. Typically, the haptic elements are attached to the base in one of two methods. The first is to drill a hole into the base, insert the haptic element into the hole, and secure it therein by a suitable method well-known to those skilled in the art, such as staking with a heat probe. The second method is to mold or manufacture the haptic elements as an integral portion of the base.

In either method, it is necessary to utilize a base to attach the haptic elements. The base increases the height of the lens and adds to the total weight of the lens.

Intraocular lenses may be implanted in either the anterior or the posterior chamber of the eye, depending on the lens design. An important consideration when the intraocular lens is to be used in the anterior chamber of the eye, is the desirability of minimizing contact of the lens with the iris. To accomplish this, the haptic elements extend outwardly and downwardly from the base of the artificial lens. This provides for a separation from the iris, but at the same time increases the overall height of the artificial lens.

In the continuing effort to reduce the height and weight of an intraocular lens, the present invention provides an artificial lens having reduced overall height compared to a prior art lens, therefore requiring a smaller incision for implantation. In addition, the entire lens is lighter in weight because the base has been substantially eliminated.

SUMMARY OF THE INVENTION

The present invention is an intraocular lens adapted for use as an artificial lens implant positioned in the posterior chamber of the eye. The intraocular lens includes an optical lens body having a first convex surface and a substantially planar second surface. The convex surface has a peripheral zone and an apex. The lens body has a height of a distance from the apex to the planar surface. A haptic element mounting means comprising a first boss is cooperatively connected to the convex surface within the peripheral zone. The first boss has a height that does not extend substantially above a plane parallel to the planar surface, the plane containing the apex of the optical lens body, whereby the boss does not substantially increase the height of the optical lens body. A first haptic element is cooperatively connected to the boss. In a preferred embodiment, the optical lens body, boss and haptic element are molded as an integral one piece unit. In a preferred embodiment, the haptic element mounting means includes a second boss cooperatively connected to the convex surface within the peripheral zone. A second haptic element is cooperatively connected to the second boss. Preferably, the first and second bosses do not extend above the plane parallel to the planar surface, the plane containing the apex of the optical lens body, whereby the bosses do not increase the overall height of the optical lens body.

In another embodiment, the intraocular lens is adapted for use as an artificial lens implant positioned in the anterior chamber of the eye. The intraocular lens includes an optical lens body having an anteriorly convex upper surface and a substantially planar bottom surface. The upper surface has a peripheral zone and an apex. The lens body has a height of a distance from the apex to the bottom surface. A haptic element mounting means comprising first and second bosses is cooperatively connected to the upper surface within a peripheral zone. The bosses have a height that does not extend substantially above a plane parallel to the bottom surface, the plane containing the apex of the optical lens body, whereby the bosses do not substantially increase the height of the optical lens body. A first haptic element is cooperatively connected to the first boss and a second haptic element is cooperatively connected to the second boss. The haptic elements extend outwardly and downwardly from the lens body, wherein the lens is supported in spaced relation anteriorly to the iris of the eye. Preferably, the first and second bosses do not extend above the plane parallel to the bottom surface, the plane containing the apex of the optical lens body, whereby the bosses do not increase the overall height of the optical lens body.

BRIEF DESCRIPTION OF THE DRAWING

FIG. 7 is a cross-sectional view of the eye and shows a second embodiment of a lens according to my present invention implanted in the anterior chamber of the eye.

FIG. 8 is a side elevtional view of the lens of FIG. 7.

FIG. 9 is a top plan view of the lens of FIG. 7.

FIG. 10 is a side elevational view of a prior art anterior chamber lens.

DESCRIPTION OF THE PREFERRED EMBODIMENT

Figure 2:
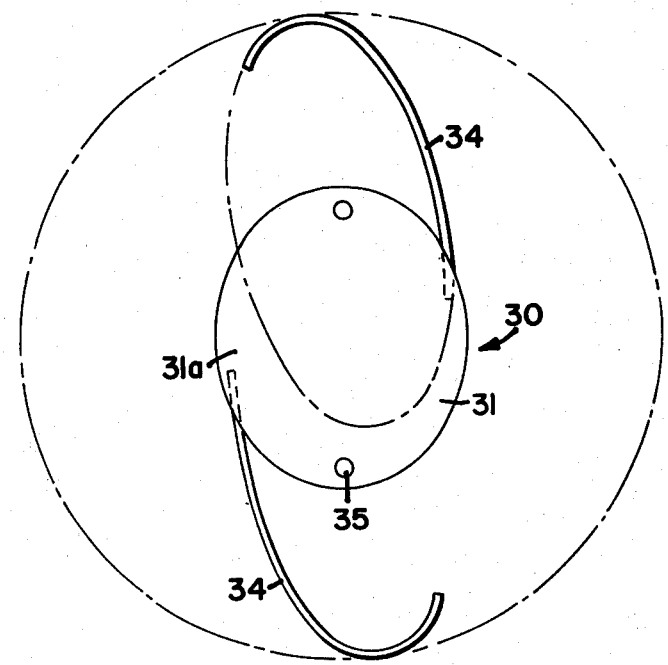
FIG. 2 is a top plan view of a prior art posterior chamber intraocular lens.
Figure 3:
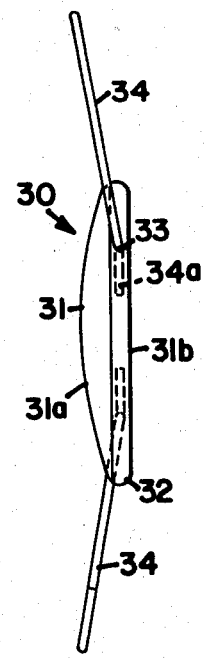
FIG. 3 is a side elevational view of the prior art lens shown in FIG. 2.

Referring to the drawing, wherein like numerals represent like parts throughout the several views, a prior art intraocular lens designated generally as 30 is shown in FIGS. 2 and 3. The intraocular lens 30 includes a lens body 31 having an anteriorly convex upper surface 31a and a substantially planar bottom surface 31b. The lens body 31 has a base 32. An aperture 33 is drilled into the base 32 and a first end 34a of a haptic element 34 is inserted into the aperture 33. The haptic element 34 is held in position by any suitable method well-known to those skilled in the art. The relatively thick base 32 is required to provide a structure to which the haptic elements 34 may be connected to the lens body 31. The base 32 adds to the height and weight of the lens 31.

Figure 1:
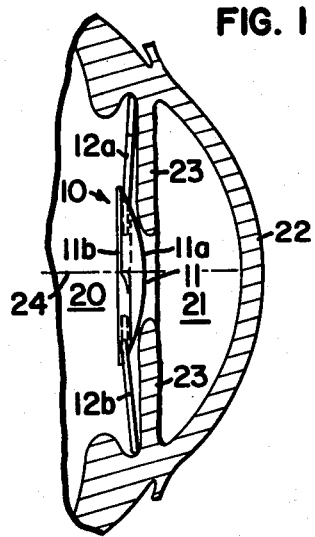
FIG. 1 is a cross-sectional view of the eye and shows a lens incorporating my present invention implanted in the posterior chamber of the eye.

An intraocular lens designated generally as 10 incorporating my present invention is shown in FIGS. 1, 4, 5 and 6. In FIG. 1, the intraocular lens 10 is shown in position in the posterior chamber of an eye. Posterior chamber 20 is separated from the anterior chamber 21 by the iris 23. The cornea 22 is in front of the anterior chamber 21.

Figure 5:
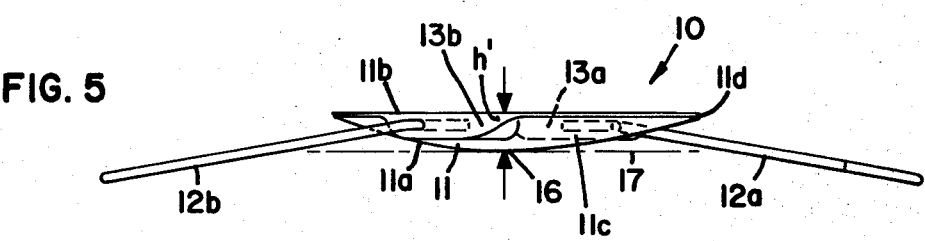
FIG. 5 is a side elevational view of the lens of FIG. 1.
Figure 4:
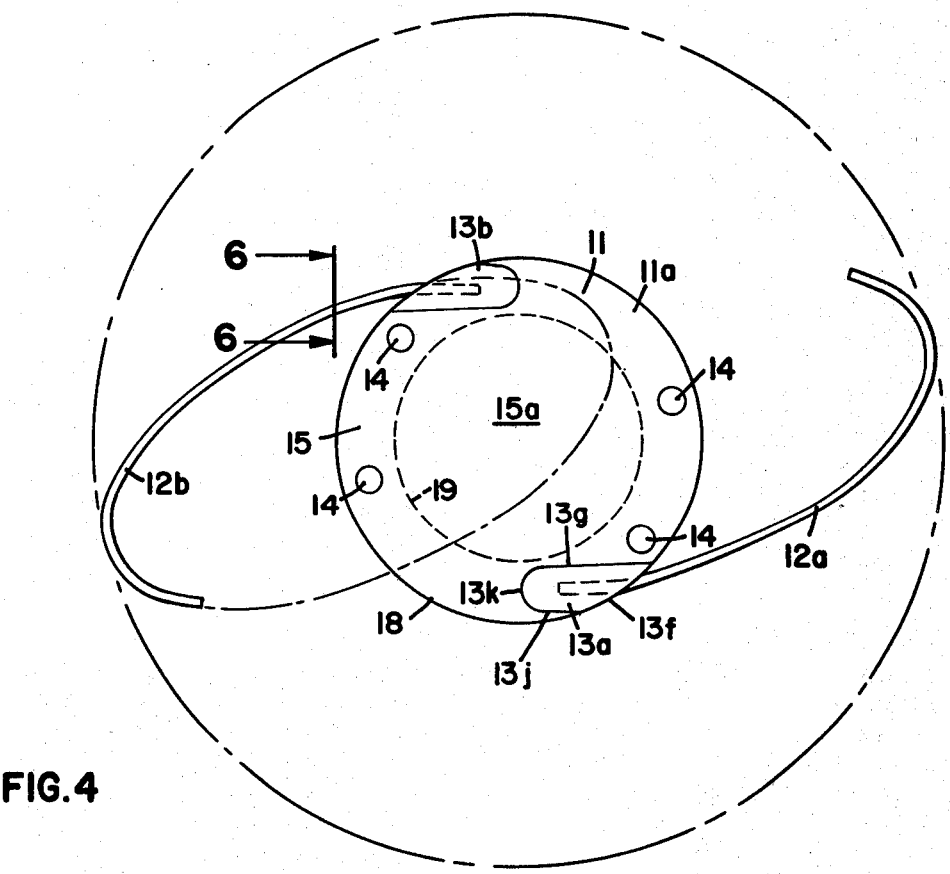
FIG. 4 is a top plan view of the lens of FIG. 1.

The intraocular lens 10 includes an optical lens body 11. The optical lens body 11 has an upper portion 11c with an anteriorly convex upper surface 11a and a base portion 11d with a posteriorly substantially planar bottom surface 11b. The base portion 11d is relatively thin compared to the upper portion 11c. The optical lens body 11 has an apex 16, a circumference 18 and an optical axis 24. The upper surface 11a has a peripheral zone 15 and is illustrated in FIG. 4 as the area between the circumference 18 of the lens body 11 and a dash separation line 19. The separation line 19 is shown for purposes of illustration only and is shown to generally indicate an outer peripheral zone. A first boss 13a is cooperatively connected to the upper surface 11a within the peripheral zone 15. The lens body 11 has a height, h', as shown in FIG. 5, of a distance between the apex 16 and the bottom surface 11b. The height h' can be characterized as the distance from the apex 16 to the bottom surface 11b measured along the optical axis 24 of lens body 11. The base portion 11d is relatively thin compared to the overall height h' of the lens body 11. A first haptic element 12a is cooperatively connected to the first boss 13a. The haptic elements 12a and 12b are located approximately across a diameter of the lens body 11. In a preferred embodiment, a second boss 13b is cooperatively connected to the upper surface 11a within the peripheral zone 15. A second haptic element 12b is cooperatively connected to the second boss 13b. The haptic elements 12a and 12b holds the intraocular lens 10 in position after it has been implanted in the eye. It is understood that other suitable combination of bosses 13a and 13b and haptic elements 12a and 12b may be used. In a preferred embodiment, the lens body 11, bosses 13a and 13b and haptic elements 12a and 12b are molded as a one piece integral unit. It is understood that haptic elements 12a and 12b may be connected to the boss 13a and 13b in any suitable manner. One alternative method would be to form an aperture in the boss 13a and insert one end of the haptic element 12a in the aperture. The haptic element 12a would be secured by any suitable method well-known in the art. Positioning holes 14 are located in the peripheral zone 15.

It is understood that doctors may alter the orientation of the lens 11 in the posterior chamber 20. That is the convex surface 11a may be posteriorly convex and the planar surface 11b may be anteriorly planar.

Figure 6:
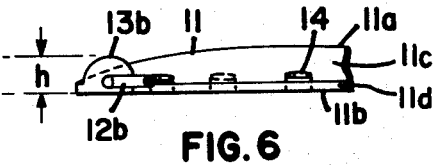
FIG. 6 is a cross-sectional view of the lens of FIG. 4, taken generally along the line 6—6 in FIG. 4.

The height, h, as shown in FIG. 6, of the bosses 13a and 13b does not extend substantially above a plane parallel to the planar surface 11b, the plane containing the apex 16 of the optical lens body 11. Such a plane is generally designated as 17 and is illustrated by the dash line in FIG. 5. The plane 17 can also be characterized as being perpendicular to the optical axis 24 of lens body 11 and containing the apex 16 of the optical lens body 11. Since the bosses 13a and 13b do not substantially extend above the plane 17, the overall height of the optical lens body 11 is not substantially increased. In a preferred embodiment, the bosses 13a and 13b do not extend above the plane 17 and the overall height of the optical lens body 11 is not increased.

The bosses 13a and 13b are cooperatively connected to the convex surface 11a within the peripheral zone 15. This provides for a unobstructed optical zone 15a. Another advantage of placing the boss 13a in the peripheral zone 15 is that the full advantage of the curvature of the lens body 11 may be utilized. By locating the bosses 13a and 13b in the peripheral zone 15, the bosses 13a and 13b may have a greater height than if they were in the optical zone 15a, and still not extend above the plane 17.

In the preferred embodiment, the boss 13a is an elongated raised portion positioned on the curved convex surface 11a within the peripheral zone 15. A longitudinal axis of the boss 13a lies along a chord of the circumference 18. A first edge 13f is co-extensive with the circumference 18. The second edge 13g and third edge 13j lie generally parallel to the longitudinal axis of the boss 13a. One end of edge 13g terminates on the outer circumference 18. Similarly, one end of third edge 13j terminates along the outer circumference 18. A fourth edge 13k connects the other ends of sides 13g and 13j. Edge 13k is curved. As shown in FIG. 6, the upper surface of boss 13b that connects second edge 13g to third edge 13j is curved surface having a convex curvature. Also, since the bosses 13a and 13b do not extend beyond the edge of base 11d, the overall circumference 18 of the optical lens body 11 is not increased.

The present invention is applicable to intraocular lenses 10 of all geometrical shapes and configurations. It is understood that any suitable material which is compatible with the environment of the eye, such as a non-toxic plastic, for example, polymethylmethacrylate may be used.

A typical height of the base 32 of a prior art lens 30 is between 0.25 to 0.30 millimeters. The overall height of the lens is approximately 1.00 to 1.05 mm for a 25 diopter lens. The present invention provides for a lens body 11 having a base 11d of approximately 0.05 mm and an overall height of approximately 0.80 mm. The improved haptic attachment for intraocular lenses of the present invention allows for the substantial elimination of the base and reduces the overall height of the lens by approximately 0.20 to 0.25 millimeters.

An example of a prior art intraocular lens adapted for use as an artificial lens implant positioned in the anterior chamber of the eye is generally designated as 36 in FIG. 10. The intraocular lens 36 is similar to the intraocular lens 30. Intraocular lens 36 includes a lens body 37 having an anteriorly convex upper surface 37a and a posteriorly planar bottom surface 37b. A base 38 has an aperture 39 though which a first end 40a of haptic element 40 is inserted. The haptic element 40 is secured in the aperture 39 by a suitable method well-known in the art. The haptic element 40 extends outwardly and downwardly from the base 38. A second portion 40b is generally parallel to the planar bottom surface 37b. When the lens 36 is implanted in the anterior chamber of the eye, the haptic elements 40 support the lens 36 in a spaced relation anteriorly to the iris of the eye.

A second embodiment of the present invention is shown in FIGS. 7, 8 and 9 and is generally designated as 50. Many of the components of the intraocular lens 50 are identical to those described with regard to intraocular lens 10. For example, the lens body 11, having an anteriorly convex upper surface 11a and a generally planar bottom surface 11b, upper portion 11c, base portion 11d, bosses 13a and 13b, peripheral zone 15, optic zone 15a, apex 16, plane 17, circumference 18, separation line 19, height h', height h and optical axis 24 are generally identical. Thus, the same reference numerals have been used in illustrating these components as were used in the first embodiment. The primary difference between the embodiment in FIGS. 7, 8 and 9 and the embodiment of FIGS. 1, 4, 5 and 6 is in a different type of haptic elements which are generally shown as 52 and 53 and the addition of third and fourth bosses 13c and 13d.

Third boss 13c and fourth boss 13d are cooperatively connected to the upper surface 11a within the peripheral zone 15. A first haptic element 52 has a first end 52a cooperatively connected to the first boss 13a. A second end 52b is cooperatively connected to the fourth boss 13d. The haptic element 52 is in the general shape of a U. First and second ends 52a and 52b extend generally outwardly and downwardly from the lens body 11. A second haptic element 53 has a first end 53a cooperatively connected to the third boss 13c and a second end 53b cooperatively connected to the second boss 13b. The haptic lement 53 is similar to the haptic element 52. When implanted in the eye, the lens 50 is supported by haptic lements 52 and 53 in a spaced relation anteriorly to the iris 23 of the eye.

In a preferred embodiment, the lens body 11, bosses 13a, 13b, 13c and 13d and haptic elements 52 and 53 are molded or manufactured as a one piece integral unit. It is understood that haptic elements 52 and 53 may be connected to the bosses 13a, 13b, 13c and 13d in any suitable manner.

While the above embodiments have been described with reference to a plano-convex lens, it is understood that the improved haptic attachment is also applicable to bi-convex lenses. The bi-convex lens would have a convex upper surface and a convex bottom surface. The bosses can be cooperatively connected to either or both of the convex surfaces.

Other modifications of the invention will be apparent to those skilled in the art in light of the foregoing description. This description is intended to provide specific examples of individual embodiments which clearly disclose the present invention. Accordingly, the invention is not limited to these embodiments or to the use of elements having specific configurations and shapes as presented herein. All alternative modifications and variations of the present invention which follows in the spirit and broad scope of the appended claims are included.

I claim:

1. An intraocular lens adapted for use as an artificial lens implant, said intraocular lens comprising:
  (a) an optical lens body having a circumference, a convex upper surface and a bottom surface, said lens body having an optical axis, said convex upper surface having a peripheral zone, an apex, and an optical zone thereinbetween, said lens body having a height of a distance from said apex to said bottom surface measured along said optical axis of said lens body; and
  (b) a haptic element mounting means, said mounting means comprising a first boss cooperatively connected to said convex surface within said peripheral zone, wherein said first boss has a height that does not extend above a plane perpendicular to said optical axis, said plane containing said apex of said optical lens body, and whereby said first boss does not substantially increase the height or circumference of said optical lens body.

2. The intraocular lens of claim 1, further comprising a first haptic element cooperatively connected to said first boss, wherein said haptic element positions and secures said lens in the eye after implantation.

3. The intraocular lens of claim 2, further comprising a second boss cooperatively connected to said convex surface within said peripheral zone and a second haptic element cooperatively connected to said second boss.

4. The intraocular lens of claim 3, further comprising third and fourth bosses cooperatively connected to said peripheral zone of said convex surface and said first haptic element having a second end cooperatively connected to said third boss and said second haptic element having a second end cooperatively connected to said fourth boss.

5. The intraocular lens of claim 1, wherein said lens body further comprises a base portion, said base portion being relatively thin compared to said height of said lens body.

6. The intraocular lens of claim 5 wherein the ratio of the thickness of the base portion to the height of the lens body is about 1:16.

7. The intraocular lens of claim 1, wherein said lens body and said boss are molded as an integral unit.

8. The intraocular lens of claim 1 wherein the longitudinal axis of said boss lies along a chord of the circumference of said lens body.

9. An intraocular lens adapted for use as an artificial lens implant positioned in the anterior chamber, said intraocular lens comprising:
  (a) an optical lens body having a circumferential edge, an upper portion having a convex upper surface and a base portion having a substantially planar bottom surface, said convex upper surface having a peripheral zone, an apex, and an optical zone thereinbetween, said lens body having a height of a distance from said apex to said bottom surface, said base portion being relatively thin compared to said upper portion; and
  (b) first, second, third and fourth bosses cooperatively connected to said peripheral zone of said upper surface, wherein said bosses do not extend beyond said edge and have a height that does not extend above a plane parallel to said bottom surface, said plane containing said apex of said optical lens body, and whereby said bosses do not increase the height or the circumference of said optical lens body; and
  (c) a first haptic element having a first end cooperatively connected to said first boss and a second end cooperatively connected to said third boss and a second haptic element having a first end cooperatively connected to said second boss and a second end cooperatively connected to said fourth boss, wherein said lens body and said bosses are formed as a one piece integral unit, said haptic elements extending outwardly and downwardly from said lens body, wherein said lens is supported in spaced relationship anteriorly to the iris of an eye.

10. The intraocular lens of claim 9 wherein the ratio of the thickness of the base portion to the height of the lens body is about 1:16.

11. The intraocular lens of claim 9 wherein the longitudinal axii of said bosses lie along chords of the circumference of the lens body.

* * * * *